US007041207B2

(12) United States Patent
Noda et al.

(10) Patent No.: US 7,041,207 B2
(45) Date of Patent: May 9, 2006

(54) SOLID ELECTROLYTE CONTAINING INSULATING GRAINS FOR GAS SENSOR

(75) Inventors: Yoshiro Noda, Gifu (JP); Ryohei Aoki, Aichi (JP); Yutaka Adachi, Aichi (JP); Yoshiaki Kuroki, Aichi (JP); Takao Kojima, Aichi (JP); Sinya Awano, Aichi (JP); Koichi Imaeda, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/251,751

(22) Filed: Sep. 23, 2002

(65) Prior Publication Data

US 2003/0034247 A1 Feb. 20, 2003

Related U.S. Application Data

(63) Continuation of application No. 09/497,645, filed on Feb. 3, 2000, now Pat. No. 6,676,817.

(30) Foreign Application Priority Data

Feb. 3, 1999 (JP) .................................. 11-26733
Dec. 28, 1999 (JP) ................................ 11-375808
Dec. 28, 1999 (JP) ................................ 11-375846

(51) Int. Cl.
*G01N 27/41* (2006.01)
*G01N 27/409* (2006.01)

(52) U.S. Cl. ....................................... 204/426; 204/424

(58) Field of Classification Search ................ 204/424, 204/425, 426, 427, 428, 429; 73/23.31, 23.32
See application file for complete search history.

(56) References Cited

U.S. PATENT DOCUMENTS 4,193,857 A 3/1980 Bannister et al.
4,221,650 A 9/1980 Friese et al.
4,224,113 A 9/1980 Kimura et al.
4,283,441 A 8/1981 Haecker et al.
4,296,148 A 10/1981 Friese
4,650,560 A * 3/1987 Ueno ......................... 204/410
4,713,166 A * 12/1987 Kojima et al. .............. 204/425
5,110,442 A * 5/1992 Kojima et al. .............. 204/426

(Continued)

FOREIGN PATENT DOCUMENTS

EP 0 942 279 A2 1/1999

(Continued)

OTHER PUBLICATIONS

Engineered Materials Handbook, vol. 4, Ceramics and Glasses, 1991, p. 1108.*

(Continued)

*Primary Examiner*—Kaj K. Olsen
(74) *Attorney, Agent, or Firm*—Sughrue Mion, PLLC

(57) ABSTRACT

A solid electrolyte layer or body capable of being co-fired with an insulating ceramic substrate or body to be used as a gas sensor laminate. The gas sensor laminate is preferably composed of an alumina substrate (1) and an oxygen-ion conductive solid electrolyte layer (6) bonded to the alumina substrate (1) by firing. The oxygen-ion conductive solid electrolyte layer or body is formed from partially or wholly stabilized zirconia, which layer contains alumina in an amount of 10% to 80% by weight, particularly 30% to 75% by weight. In this manner, another ceramic layer; particularly, a ceramic layer (7) of alumina can further be bonded to the oxygen-ion conductive solid electrolyte layer. The relative density of the ceramic layer can be 60% to 99.5%, preferably 80% to 99.5%.

20 Claims, 9 Drawing Sheets

8
7
5
5 a
6
4 a
4
2 b
2 a
1 b
1
1 a
3
3 a
3 b

U.S. PATENT DOCUMENTS

| | | | | |
|---|---|---|---|---|
| 5,329,806 | A | 7/1994 | McClanahan et al. | |
| 5,447,618 | A | 9/1995 | Sugiyama et al. | |
| 5,573,650 | A | 11/1996 | Fukaya et al. | |
| 5,660,661 | A | 8/1997 | Sugiyama et al. | |
| 5,849,165 | A | 12/1998 | Kojima et al. | |
| 5,895,591 | A * | 4/1999 | Kojima et al. | 219/209 |
| 5,968,673 | A * | 10/1999 | Aizawa et al. | 428/688 |
| 5,998,012 | A | 12/1999 | Friese et al. | |

FOREIGN PATENT DOCUMENTS

| | | |
|---|---|---|
| GB | 2 054 167 B | 3/1984 |
| JP | 54-145713 | 11/1979 |
| JP | 61-51557 | 3/1986 |
| JP | 61-172054 | 8/1986 |
| JP | 62-88954 | 4/1987 |
| JP | 6-300731 | 10/1994 |
| JP | 8-201337 | 8/1996 |
| JP | 11-118758 | 4/1999 |
| JP | 11-160274 | 6/1999 |

OTHER PUBLICATIONS

Aldrich Chemical Catalog, 1994, p. 51.*

Charles Lynch, ed. "Practical Handbook of Materials Science", pp. 299, 310, 311. 1989.

Liu et al. "Oxygen Sensors", from Engineered Materials Handbook, vol. 4, Ceramics and Glasses. pp. 1131-1139. 1991.

European Search Report for EP 00 30 0860 dated Aug. 23, 2004.

* cited by examiner

SOLID ELECTROLYTE CONTAINING INSULATING GRAINS FOR GAS SENSOR

CROSS REFERENCE TO RELATED APPLICATIONS

This is a continuation of Application Ser. No. 09/497,645 filed Feb. 3, 2000 now U.S. Pat. No. 6,676,817; the disclosure of which is incorporated herein by reference.

BACKGROUND OF THE INVENTION

1. Field of the Invention

The present invention generally relates to an electrolyte, particularly to an electrolyte body or layer for use in a cell that flows or rather transfers ions such as oxygen ions, lithium ions, sodium ions between the electrodes of the cell. Specifically the invention provides a gas sensor with a solid electrolyte for detecting or rather measuring a concentration of a specific gas component such as $O_2$, $CO_2$, $NO_x$, HC, $H_2O$ and $H_2$. More specifically, this invention provides a gas sensor with an electrochemical cell using an oxygen ion conductive solid electrolyte that is capable of transferring or conducting oxygen to thereby detect a specific gas component existing in an exhausted gas emitted from an internal combustion engine, and a method for fabricating the gas sensor. Further, the invention provides a new oxygen-ion conductive solid electrolyte material and a strenuous gas-sensor structure using the same.

2. Description of the Related Art

Conventionally, various gas sensors using a solid electrolyte such as zirconia have been proposed for internal combustion engine control. For instance, a so-called lambda sensor that employs a cylindrical and bottom-closed solid electrolyte has been widely used for detecting oxygen in a gas exhausted from an internal combustion engine. On the other hand, a so-called thick-film gas sensor that utilizes a thick electrolyte film or rather layer formed on a ceramic substrate or rod as a sensing element has been proposed, which sensor enables prompt activation of a gas-sensing mechanism as compared to the lambda sensor. This is because its heat-propagation efficiency is comparatively high compared to the lambda sensor. The thick-film gas sensor may include an insulating ceramic substrate or rod in which a heating wire is embedded and insulated from the electrolyte film, and which substrate is co-fired with the electrolyte film so as to form an integral or unitary ceramic laminate as a gas sensor.

In a conventional process of fabricating the thick-film gas sensor, a green or rather unfired oxygen-ion conductive solid electrolyte layer including zirconia particles therein and unfired metal electrode wires formed thereon is superposed on an unfired alumina substrate, and then the layer and the substrate are co-fired to form the unitary laminate. However, this process encounters a problem in that since the alumina substrate and the zirconia differ in thermal coefficient and thermal expansion and the zirconia undergoes a phase transition with firing temperature variations, a volume change and/or thermal stress is induced in the laminate. This causes difficulties in attaining a high-quality oxygen-ion conductive solid electrolyte layer of zirconia firmly bonded on the alumina substrate without losing the required performance by co-firing. Otherwise, cracks are induced in the resultant oxygen-ion conductive solid electrolyte layer formed on the laminate in a thermal cycle environment ranging, e.g., from −20° C. up to 1100° C. (hereinafter referred to as “thermal cycle”).

Suppression of cracking in the laminate and firmly bonding the oxygen-ion conductive solid electrolyte layer thereon are disclosed in Japanese Patent Application Laid-Open (kokai) Nos. 61-51557, 61-172054, and 6-300731. However, these disclosures are still unsatisfactory in bringing about a good solid electrolyte ceramic that can be used as a thick film layer of a gas sensing element formable with an insulating ceramic substrate or rod.

SUMMARY OF THE INVENTION

It is therefore an object of the present invention to solve the above-mentioned problems and to provide a new or improved electrolyte body or layer capable of sufficiently suppressing the formation of cracks during fabrication and/or use including use in a high temperature gas environment.

Another object of the invention is to provide a tough laminate comprised of an electrolyte ceramic layer and a ceramic substrate, for use in a gas sensor.

Yet another object is to provide a method of fabricating a solid electrolyte body, layer and/or laminate that withstands and perform well in a high temperature gas environment.

In terms of practical applications of a solid electrolyte of zirconia including a partially or wholly stabilized one, it has been conventionally believed that inclusion of insulating ceramic material into the solid electrolyte material should be less than about 5% by mass (=% by weight). Otherwise, such alumina inclusion degrades the electrochemical function of the fired solid electrolyte.

However, the present inventors have found that, even if the solid electrolyte ceramic contains the insulating ceramic grains in a remarkably increased amount, e.g., several tens of percent by weight (namely, 10–80% by weight), the fired solid electrolyte having such a large amount of the insulating grains therein can function sufficiently as a solid electrolyte for a gas sensor cell and is comparable to a conventional one containing alumina in an amount of less than 10% by weight. Especially when a laminate is formed using a partially or wholly stabilized zirconia electrolyte containing several tens of percent of alumina grains of high purity, according to the invention, the laminate works better in some physical values than a conventional one that contains a lesser amount of alumina.

Specifically, an average grain size of the oxygen-ion conductive solid electrolyte other than the insulating grains after firing becomes not more than 2.5 μm, according to the invention, when an average particle size of the alumina, zirconia and yttria powders contained in a green or rather unfired body or layer is less than 1 μm.

These findings are quite useful for developing a good solid electrolyte body and/or a thick-film laminated structure (namely a laminate of at least one electrolyte layer and another material layer) for use in a high temperature gas sensor. Typically, such a laminate has a total thickness of 10 μm–150 μm at an electrolyte portion that is coated or bonded integrally on a thick strenuous insulating substrate or rod of alumina by co-firing. The alumina substrate is preferred when alumina grains with high purity is included in the electrolyte portion that is coated or bonded with metal electrodes such as platinum, forming the laminate of a gas sensor.

According to a first aspect of the first embodiment according to the invention, a solid electrolyte ceramic body is provided containing insulating ceramic grains and partially or wholly stabilized electrolyte ceramic, wherein the ceramic body contains 10% to 80% by weight of the insulating ceramic grains having an average grain size of not larger than 1 μm distributed in the partially or wholly stabilized electrolyte ceramic. The rest in the insulating body, in other words, more than 20% by weight of the ceramic body is the partially or wholly stabilized electrolyte. Herein, it is important, when the electrolyte is used for a cell for a gas sensor, that the electrolyte body is formed so that the stabilized zirconia grains are continuously connected to each other in a manner surrounding the insulating grains. Otherwise, the cell having electrodes cannot transfer ions from one electrode to another. If the average grain size of the insulating ceramic grains are formed, a mechanical or electrical performance of the electrolyte body tends to be lost.

In a second aspect of the first embodiment, the solid electrolyte ceramic body importantly has insulating ceramic grains having an average purity of more than 99%. The preferable purity of the insulating ceramic grain is more than 99.9% and the most preferable purity is more than 99.99% or more than 99.995% when it is measured at the center of the grain, because high-purity insulating grains tend not to combine with other ceramic material. Although there are various candidates for the high-purity insulating grains, alumina grains having such purity as described above are best in the case that the solid electrolyte ceramic is required to transfer oxygen-ions therethrough. The reason is that the alumina ($Al_2O_3$) per se has oxygen.

A high-purity alumina powder of more than 99.9% purity is included in a green body or layer that otherwise consists substantially of electrolyte ceramic such as zirconia and hafnia, an inorganic stabilizer such as yttria and magnesia and some organic binder is used in forming a good oxygen-ion conductive solid electrolyte ceramic according to the invention. The purity of insulating grains, specifically alumina grains is important in order to prevent not only electrical or mechanical degradation of the solid electrolyte (fired) in use but also in fabrication thereof. A far better performance of the solid electrolyte is attained when the purity of the alumina powder included in the unfired electrolyte layer is more than 99.99% or particularly preferably more than 99.995%.

Another important factor is the purity of the zirconia powder and yttria mixed therewith. Foreign contaminating material other than zirconia and yttria should be less than 1% by weight, preferably not more than 0.1% by weight, or more preferably not more than 0.05% by weight.

In a third aspect of the first embodiment, the solid electrolyte ceramic body has a partially or wholly stabilized solid electrolyte that contains 20% to 90% by weight of partially or wholly stabilized zirconia having a purity of more than 99% or preferably more than 99.9%. When the partially or wholly stabilized solid electrolyte contained inside the ceramic body has a form of solidified grains having an average grain size of not greater than 2.5 μm, the mechanical or electrical performance of the solid electrolyte ceramic body or layer is enhanced, particularly with the alumina grains.

Specifically, the specific resistance of the oxygen-ion conductive ceramic body or layer measured at 800° C. becomes less than 10-Ωm in a range of up to 80% by weight of the insulating ceramic grains contained with the partially or wholly stabilized zirconia formed inside the ceramic body. More specifically, the specific resistance of the electrolyte ceramic body substantially consisting of 30–70% of the alumina grains and 30–70% of the remainder of partially stabilized zirconia (yttria-partially stabilized zirconia), measured at 800° C. becomes remarkably less than 5-Ωm which is comparable with that of a conventionally known solid electrolyte ceramic body containing substantially less than 20% of unpurified insulating ceramic other than zirconia and yttria inside the electrolyte, measured under the same condition.

When unpurified or contaminated insulating ceramic such as less than 99%—purity alumina is incorporated into the electrolyte body of partially or wholly or stabilized zirconia, the specific resistance increases remarkably more than an order of 20 Ω-m to more than 1000 Ω-m when inclusion of such unpurified ceramic increases only from 10% to 20% by weight, when the specific resistance is measured at a temperature of 800° C. in the ambient atmosphere. The reason is that a contaminating material in the alumina together with the alumina blocks or hinders ions such as oxygen ions passing through the zirconia electrolyte formed inside the body.

On the other hand, when a high-purity alumina and a high purity-zirconia and a high-purity yttria are used in accordance with a teaching of this invention that will hereinafter be more specifically disclosed, the specific resistance of the electrolyte body according to the invention is less than 0.1 Ω-m by the inclusion of less than 10% by weight of the high purity alumina, and about less than 5 Ω-m by the inclusion of 10–50% by weight of the same alumina. It is very surprising that by incorporation of such a high amount of 30–70% by weight of the same high-purity alumina into the electrolyte body according to the invention, the specific resistance value exhibits low values of only several Ω-m, less than 20 Ω-m or less than 40 Ω-m. Herein, the specific resistance is measured based on the well known Cole-Cole plot method on the electrolyte ceramic body with two electrodes formed therebetween at a temperature of 800° C. in the ambient atmosphere.

As described above, incorporation of high-purity alumina grains into the solid electrolyte does not so degrade its electrical performance needed for electrical applications such as a gas sensor. In addition, this can advantageously change other physical values such as thermal expansion coefficient and mechanical strength by varying a percentage of the alumina inclusion so as to match with other bodies or layers such as a metal layer, insulating ceramic substrate or layer and even a metal layer.

There is a great advantage of laminating a plurality of solid electrolyte bodies and/or layers, each having a different percentage of high purity insulating grains, because different physical parameters (electrical, chemical or mechanical properties) are attained by each of the electrolyte bodies or layers. Each body or layer may have a metallic electrode forming a electrochemical cell, may have cermet electrodes including some metal and ceramic, or may have an insulator bonded therewith.

The present invention can be applied to various electrolyte-using cells such as a lithium or sodium-ion conducting cell and ion-separator including a polymer or solid ceramic electrolyte, so long as inclusion of high-purity insulating ceramic grains does not cause a serious problem in those cells or separator. The cell or separator as used herein means that only a specific ion such as oxygen and lithium passes therethrough but does not allow other ions to pass.

According to a first aspect of a second embodiment embodiment according to the present invention, a gas sensor is provided with an electrochemical cell for detecting a gas concentration, comprising an oxygen-ion conductive solid electrolyte layer; and metallic electrodes formed on the oxygen-ion conductive solid electrolyte layer; wherein the oxygen-ion conductive solid electrolyte layer contains 10% to 80% by weight of insulating ceramic grains.

The above gas sensor may further advantageously comprise an alumina substrate on which the oxygen-ion conductive solid electrolyte layer is formed integrally, a heater disposed within the alumina substrate; an oxygen-reference electrode formed integrally on the oxygen-ion conductive solid electrolyte layer; and a gas-measuring electrode formed integrally on the oxygen-ion conductive solid electrolyte layer, wherein the oxygen-ion conductive solid electrolyte layer contains zirconia and alumina grains such that the alumina grains contained in the oxygen-ion conductive solid electrolyte layer account for 10% to 80% by weight or more advantageously 20% to 75% based on the total weight of the oxygen-ion conductive solid electrolyte layer. In this sensor, when the content of the alumina grains is 30% to 70% by weight based on the weight of the oxygen-ion conductive solid electrolyte layer the requirements of most oxygen-ion based gas sensors used with internal combustion engine which elevate the sensor temperature and vibrate the sensor, such as an oxygen sensor, NOx sensor and HC sensor can be satisfied.

In addition, the gas sensor may further comprise an intermediate layer disposed between the alumina substrate and the oxygen-ion conductive solid electrolyte layer, wherein the intermediate layer contains the zirconia and insulating ceramic such that the insulating ceramic content of the intermediate layer is different from that of the oxygen-ion conductive solid electrolyte layer. In this configuration, good performance of the high temperature sensor is attained. Further improvement is expected when the content of the insulating ceramic contained in the intermediate layer is at least 10% by weight greater than that of the insulating ceramic contained in the oxygen-ion conductive solid electrolyte layer. The best main material contained in the insulating ceramic substrate is high purity-alumina.

Another ceramic layer having a relative density of 60% to 99.5% may be formed on the gas-measuring electrode and/or the oxygen-ion conductive solid electrolyte layer. On such a ceramic layer having a density as described above, a poison-prevention layer such as spinel layer may be formed on an outside surface of the ceramic layer for preventing the gas-measuring electrode from being poisoned by a foreign element such as Pb.

The insulating grain contained in the oxygen-ion conductive solid electrolyte layer in the above configuration of the gas sensor is importantly a product formed from alumina of more than 99.9% purity, or of more than 99.99% purity.

According to a second aspect of the second embodiment, a gas sensor is provided with an electrochemical cell for detecting or measuring a gas, comprising: an insulating ceramic substrate and a oxygen-ion conductive solid electrolyte layer formed integrally on the substrate by firing, wherein the oxygen-ion conductive solid electrolyte layer contains zirconia and the insulating ceramic such that, when the total amount of zirconia and insulating ceramic is taken as 100% by weight, the insulating ceramic accounts for 10% to 80% by weight. The insulating ceramic substrate is alumina in a shape of, e.g., a cylindrical column or rod on which the oxygen-ion conductive solid electrolyte layer is formed integrally; a heater disposed within the alumina column or rod; an oxygen-reference electrode formed integrally on the oxygen-ion conductive solid electrolyte layer; and a gas-measuring electrode formed integrally on the oxygen-ion conductive solid electrolyte layer, wherein the oxygen-ion conductive solid electrolyte layer contains zirconia and alumina grains such that the alumina grains contained in the oxygen-ion conductive solid electrolyte layer account for 10% to 80% by weight based on the total weight of the oxygen-ion conductive solid electrolyte layer.

Any insulating ceramic material for the “substrate” (or rod) can be used so long as it is stable at high temperature and shows insulating properties. Although not particularly limited, good examples of such insulating ceramic material are alumina, mullite, and spinel when the “electrolyte ceramic” is oxygen-ion conductive. Among them, an alumina substrate is best, because a wire for heating the electrolyte can be co-fired to be embedded within the alumina substrate when all others parts are co-fired (simultaneously fired) to form a laminate for a gas sensor element.

The oxygen-ion conductive solid electrolyte layer contains “electrolyte ceramic” and “insulating ceramic”, wherein the insulating ceramic accounts for 10% to 80% by weight, according to this aspect of the invention. The oxygen-ion conductive solid electrolyte layer is integrally or rather unitarily formed on the insulating substrate (including rod) so as to form a sturdy laminate capable of being held firmly in a housing of a conventionally known gas sensor which is often subjected to a severe vibrant environmental condition.

Since the oxygen-ion conductive solid electrolyte layer according to the invention contains insulating ceramic as one of main components, when the electrolyte layer is unitarily bonded with the ceramic substrate by co-firing to form a ceramic laminate, a thermal stress that arises between the substrate and the oxygen-ion conductive solid electrolyte layer due to their difference in coefficient of thermal expansion is extremely alleviated thereby sufficiently suppressing cracking or delamination in the laminate.

By employing the insulating ceramic falling within the above range, growth of zirconia grains in the oxygen-ion conductive solid electrolyte layer is effectively inhibited, thereby suppressing the phase transition of zirconia which would otherwise result from exposure to temperature variations involved in the firing or thermal cycle. Even when the phase transition occurs partially, cracking can be suppressed since stress is readily dispersed.

As described above, the oxygen-ion conductive solid electrolyte layer contains insulating ceramic in an amount of 10% to 80% by weight. When the insulating-ceramic content is less than 10% by weight, cracking in the oxygen-ion conductive solid electrolyte layer is not suppressed sufficiently, potentially resulting in separation of the oxygen-ion conductive solid electrolyte layer from the insulating substrate, particularly at an edge portion. When an insulating-ceramic content in the oxygen-ion conductive solid electrolyte layer used with the insulating substrate is in excess of 80% by weight, oxygen ion conductivity of the oxygen-ion conductive solid electrolyte layer decreases to a unusable range. The insulating-ceramic content is preferably 20% to 75% by weight, more preferably 30% to 70% by weight for a laminated configuration of the gas sensor element.

The insulating-ceramic or zirconia content in the oxygen-ion conductive solid electrolyte layer can be obtained not only by conventional chemical analysis, but also by image analysis of electron photomicrographs. For example, a BEI image (back scattered electron image) photographed by an SEM (scanning electron microscope) is scanned by means of a scanner to obtain electronic information regarding the image. On the basis of the electronic information, an area ratio between insulating-ceramic grains and zirconia grains contained in the electrolyte layer is determined by use of an image analyzer (for example, LUZEX FS, product of NIRECO). On the basis of the thus-obtained area ratio, a theoretical volume ratio is calculated through approximation, and the thus-obtained volume ratio is converted to a content by weight of the insulating ceramic.

Zirconia contained in the oxygen-ion conductive solid electrolyte layer is preferably in the form of stabilized zirconia or partially stabilized zirconia. If physical properties such as mechanical strength, toughness, and thermal-impact resistance of the oxygen-ion conductive solid electrolyte layer formed on the insulating ceramic substrate are required to be optimized, the zirconia partially stabilized by yttria of 2 to 9% by mole, more preferably 4% to 8% by mole is recommended to be mixed with the insulating ceramic of high purity-alumina to form the best electrolyte layer according to the invention. Other stabilizers may be magnesia and calcia.

According to a third aspect of the second embodiment, the gas sensor may further comprise an intermediate layer disposed between the insulating substrate and the oxygen-ion conductive solid electrolyte layer, the intermediate layer containing zirconia and insulating ceramic. A preferable amount of the insulating ceramic contained in the intermediate layer is at least 10% by weight (more preferably, at least 15% by weight) greater than that of the oxygen-ion conductive solid electrolyte layer. By employing such an intermediate layer, the substrate and the oxygen-ion conductive solid electrolyte layer having electrodes for use as a cell can bond to each other more firmly by co-firing. A plurality of the intermediate layers may be employed. The intermediate layer may be used as a cell in part or whole by forming at least one electrode on the intermediate layer, since the intermediate layer contains electrolyte ceramic other than insulating ceramic. Preferably, the intermediate layer that directly contacts the insulating ceramic substrate (or rod) may contain alumina and zirconia such that the amount ratio of alumina to zirconia is the highest among the intermediate layers. The intermediate layer in direct contact with the oxygen-ion conductive solid electrolyte layer may contain alumina and zirconia such that the amount ratio of zirconia to alumina is the highest among the intermediate layers. In these configurations according to the invention, the stress induced by phase transition and temperature shift between the outermost layer and the substrate is much decreased.

According to a fourth aspect of the second embodiment, the insulating ceramic contained in the substrate, the oxygen-ion conductive solid electrolyte layer or the intermediate layer is preferably alumina. This is because alumina is stable at high temperature; has excellent mechanical strength, heat resistance, and insulating properties; and yields excellent bonding strength in bonding with the oxygen-ion conductive solid electrolyte layer by co-firing.

According to a fifth aspect of the second embodiment, at least two electrode layers may be formed on the oxygen-ion conductive solid electrolyte layer, to thereby use the gas sensor element as, for example, a monolithic gas sensor element. A pair of electrode layers may be formed on the same side of the oxygen-ion conductive solid electrolyte layer or on the respective opposite sides of the oxygen-ion conductive solid electrolyte layer.

According to a sixth aspect of the second embodiment, a ceramic layer having a relative density of 60% to 99.5% is formed on the outermost oxygen-ion conductive solid electrolyte layer. According to a seventh aspect of the second embodiment, a ceramic layer having a relative density of 60% to 99.5% may be formed on both the oxygen-ion conductive solid electrolyte layer and electrodes or between the electrolyte layer and the intermediate layer, thereby further effectively suppressing or preventing cracking in the gas sensor element (including oxygen-ion conductive solid electrolyte layer).

According to a first aspect of a third embodiment according to the invention, a method of fabricating a gas sensor is provided, comprising: forming a powder mixture of alumina, zirconia and yttria; disposing two unfired metallic electrodes on a unfired layer formed from the mixture; and firing the layer, the two unfired electrodes and an insulating substrate simultaneously at a temperature of from 1350° C. to 1600° C. so as to form a ceramic laminate having an oxygen-ion conducting cell having an oxygen-ion conductive layer that is capable of transferring oxygen-ions between the fired electrodes, wherein the oxygen-ion conductive solid electrolyte layer contains from 10% to 80% by weight of alumina grains and 20 to 90% by weight of zirconia stabilized partially or wholly by yttria.

In the above method, the zirconia and yttria constituting the powder mixture may be advantageously those attained by co-precipitating a liquid that contains an alkoxide of zirconium and an alkoxide of yttrium, since a uniformly mixed powder is attained by co-precipitation. It is important to produce a contamination free mixture such as a less than 0.1 percent contaminated mixture for the mixture of zirconia and stabilizer for use in the method of the invention. In other words, the zirconia and yttria powders are those uncontaminated at a purity level of more than 99.9%.

More important may be the purity of the alumina grains to be mixed with the mixture of zirconia and stabilizer. The purity of the alumina powder is more than 99.9% or more preferably 99.99% in the method according to the invention, because there is a tendency that such high purity alumina particles do not form a solute with the zirconia or yttria during firing and do not cause the internal resistance of the electrolyte to rise too high for a gas sensor.

According to a second aspect of the third embodiment, a method of fabricating a laminate for a gas sensor (i.e., gas-sensing element) is provided, comprising: (1) forming a unfired ceramic layer that contains zirconia powder and insulating ceramic powder such that an amount of the insulating ceramic powder becomes 10% to 80% by weight compared to a total amount of the zirconia and insulating ceramic powder contained in the unfired layer; (2) superposing the unfired ceramic layer on an insulating ceramic layer so as to form a unfired ceramic laminate; and (3)integrally firing the unfired ceramic laminate to form a fired oxygen-ion conductive solid electrolyte layer at an outermost surface of a resultant fired ceramic laminate so that a grain size of the fired solid electrolyte becomes less than 2.5 μm.

With respect to the above method according to the second aspect, it is much preferred to use fine zirconia powder having an average particle size of less than 1 μm which is attained through precipitation, so as to attain a grain size of the fired solid electrolyte that is less than 2.5 μm. It is best to use fine zirconia powder containing a stabilizer powder selected from yttria (yttrium oxide), magnesia (magnesium oxide) and/or calcia, the stabilizer-containing zirconia powder being made by co-precipitation as described above.

The phrase "integrally firing" or the word "co-firing" means performing the steps of: superposing at least one unfired oxygen-ion conductive solid electrolyte layer or body on another unfired layer, substrate or body of ceramic or metal; and firing the resultant laminate into a single unit. The insulating ceramic is not particularly limited, and examples thereof include alumina, mullite and spinel. In view of stability at high temperature, mechanical strength, heat resistance and insulating properties, alumina is most preferred as the insulating ceramic.

According to a third aspect of the third embodiment, "firing" is performed preferably at a temperature of 1350° C. to 1600° C. (more preferably, 1400° C. to 1550° C.). At a firing temperature lower than 1350° C., the fired laminate fails to be sufficiently fired; in other words, a uniformly sintered laminate is hardly obtained. At a firing temperature higher than 1650° C., grains formed inside the electrolyte layer grow anomalousy. Firing at the above temperature range is maintained preferably for 0.5 hour to 6 hours (more preferably, 1 hour to 2 hours).

According to a fourth aspect of the third embodiment, a powder material substantially consisting of zirconia and stabilizer is advantageously used, which powder is attained by co-precipitation and contains the zirconia and a stabilizer. By co-precipitation, the stabilizer and zirconia are mixed uniformly, and zirconia material powder having a small grain size; specifically, an average grain size not greater than 1.0 μm is readily attained. Examples of such a stabilizer include yttria, magnesia and calcia.

The "measuring electrode" and "oxygen-reference electrode" may be formed on corresponding opposite sides of the oxygen-ion conductive solid electrolyte layer; for example, by a step of printing an electrode pattern using a platinum-containing paste, followed by firing. Alumina and/or zirconia stabilized in part or whole may be added to the platinum-containing paste. The oxygen-reference electrode and the measuring electrode may be formed on the corresponding opposite sides of the oxygen-ion conductive solid electrolyte layer. A gas under measurement comes into contact with the measuring electrode, while a oxygen-concentration reference gas comes into contact with the oxygen-reference electrode. As a result, an electromotive force is induced according to an oxygen concentration difference between the electrodes by an oxygen concentration cell effect based on the Nernst equation.

The "heater" disposed within the substrate is adapted to heat the oxygen-ion conductive solid electrolyte layer and comprises a heating portion and a heater lead portion for the heating portion. The heater lead portion connects the heating portion and lead wires so that an electrical current or voltage is applied across the wires so as to heat the heating portion. In the gas sensor element having the heater, heat generation characteristics of the heater are determined by the resistance of the material for the heater, which is desired to be adjusted widely by controlling or varying the firing temperature. The gas sensor element made according to the method of the present invention allows a wide firing temperature range of 1350° C. to 1600° C. in the course of fabrication thereof. In other words, when the heater portion, the unfired substrate, and the unfired oxygen-ion conductive solid electrolyte layer are co-fired, the resistance of the heater can be advantageously controllable in a wide range of plus or minus 50% or so to a target value, due to use of the solid electrolyte containing alumina grains according to the invention.

According to a fifth aspect of the third embodiment, a gas sensor is provided comprising: an insulating ceramic substrate and a oxygen-ion conductive solid electrolyte layer formed integrally on the substrate; a heater disposed within the insulating ceramic substrate; an oxygen-reference electrode formed on a side of the oxygen-ion conductive solid electrolyte layer that contacts the substrate; and a measuring electrode for detecting a gas formed on the other side of the oxygen-ion conductive solid electrolyte layer, wherein the oxygen-ion conductive solid electrolyte layer contains zirconia and insulating ceramic such that, when the total amount of zirconia and insulating ceramic is taken as 100% by weight, the insulating ceramic accounts for 10% to 80% by weight.

The "substrate", "oxygen-ion conductive solid electrolyte layer" and the "zirconia" content and "insulating ceramic" content in the fired oxygen-ion conductive solid electrolyte layer may be similar to those in the other aspects described previously so as to yield similar effects. The oxygen-ion conductive solid electrolyte layer may contain alumina grains preferably in an amount of 20% to 75% by weight or preferably 30% to 75% by weight therein.

The gas sensor element may further comprise an intermediate layer disposed between the substrate and the oxygen-ion conductive solid electrolyte layer and/or between the substrate and the oxygen-reference electrode, the intermediate layer containing zirconia stabilized in part or whole and insulating ceramic. The intermediate layer contains zirconia and insulating ceramic such that, when the total amount of zirconia and insulating ceramic is taken as 100% by weight, the insulating ceramic content of the intermediate layer is preferably at least 10% by weight (more preferably, at least 15% by weight) greater than that of the oxygen-ion conductive solid electrolyte layer. In this manner, the intermediate layer can have a thermal expansion coefficient falling between those of the substrate and oxygen-ion conductive solid electrolyte layer, thereby more reliably suppressing cracking in the oxygen-ion conductive solid electrolyte layer. Further, since the insulating-ceramic content of the intermediate layer falls between that of the substrate formed of insulating ceramic and that of the oxygen-ion conductive solid electrolyte layer which contains insulating ceramic in an amount of 10% to 80% by weight, the substrate and the oxygen-ion conductive solid electrolyte layer is bonded more firmly via the intermediate layer with less stress preventing delamination or cracks.

Particularly, when the insulating-ceramic content of the oxygen-ion conductive solid electrolyte layer is considerably low compared to that of the insulating substrate, two or more intermediate layers may be employed. In such a case, the insulating-ceramic content of the intermediate layer may be reduced sequentially such that the intermediate layer in contact with the substrate (such as an alumina substrate) has the highest insulating-ceramic content (alumina content), while the intermediate layer in contact with the oxygen-ion conductive solid electrolyte layer has the lowest insulating-ceramic content, thereby more effectively suppressing cracking in the oxygen-ion conductive solid electrolyte layer. Also, the substrate and the oxygen-ion conductive solid electrolyte layer can be bonded far more firmly via the two or more intermediate layers of different insulating-ceramic contents. The intermediate layers may be formed so as to extend over the entire surface of the substrate. Alternatively, in the case of a gas sensor of a reference-gas introduced type other than a self-reference gas formed type, the intermediate layer in contact with the oxygen-ion conductive solid electrolyte layer or all of the two or more intermediate layers may be formed to have a reference-gas introducing passage therein.

The thickness of the intermediate layer (when two or more intermediate layers are involved, the total thickness of the intermediate layers is counted) is preferably 5 μm to 200 μm, more preferably 20 μm to 50 μm. When the thickness of the intermediate layer is less than 5 μm, the intermediate layer fails to sufficiently suppress cracking in the oxygen-ion conductive solid electrolyte layer, resulting in a failure to bond firmly the substrate and the oxygen-ion conductive solid electrolyte layer. In the case of a gas sensor element, when the thickness of the intermediate layer is in excess of 200 μm, heat transmission to the oxygen-ion conductive solid electrolyte layer from the heater disposed within the substrate of insulating ceramic is delayed, potentially failing to activate promptly the oxygen-ion conductive solid electrolyte layer through efficient heating. Also, an excessively thick intermediate layer may cause cracking in the oxygen-ion conductive solid electrolyte layer due to thermal strain.

According to a sixth aspect of the third embodiment, the insulating ceramic to be contained in the substrate and the oxygen-ion conductive solid electrolyte layer or in the intermediate layer is preferably alumina. This is because alumina is stable at high temperature; has excellent mechanical strength, heat resistance and insulating properties; and yields excellent bonding strength in bonding with the oxygen-ion conductive solid electrolyte layer.

According to a seventh aspect of the third embodiment, a ceramic layer having a relative density of 60% to 99.5% (preferably 80% to 99.5%) may be bonded to the measuring electrode on the side opposite the substrate, thereby effectively suppressing cracking in the oxygen-ion conductive solid electrolyte layer. In the case of a ceramic layer having a relative density of less than 60%, even when a poisoning prevention layer is provided, poisoning of the measuring electrode with Pb, Si or P may not be suppressed or prevented sufficiently. When the relative density is in excess of 99.5%, oxygen contained in the gas under measurement fails to reach the measuring electrode promptly and sufficiently; as a result, the responsiveness of the gas sensor element tends to be impaired.

The thickness of the ceramic layer is 10 μm to 200 μm, preferably 20 μm to 100 μm, more preferably 25 μm to 70 μm. When the thickness of the ceramic layer is less than 10 μm, the ceramic layer fails to sufficiently protect the measuring electrode and fails to sufficiently strengthen the gas sensor element as a whole.

The poisoning prevention layer for protecting the electrode may be made of spinel. When the poisoning prevention layer is to be formed, a portion of the ceramic layer corresponding to the poisoning prevention layer may be formed by applying a slurry so as to be a relatively thin layer. The other portion of the ceramic layer may be formed of a sheet having a thickness substantially equal to that of the poisoning prevention layer so as to be a relatively thick layer. Thus, the resultant gas sensor element does not involve any stepped portion which would otherwise cause stress concentration.

In the case of a gas sensor element of a reference-oxygen self-generation type (that may be called a ICP type), the thickness of the oxygen-ion conductive solid electrolyte layer is preferably not less than 10 μm up to 70 μm (more preferably 20 μm to 60 μm, most preferably 30 μm to 50 μm). When the thickness is less than 10 μm, the durability of the oxygen-ion conductive solid electrolyte layer may become insufficient. In order to form a thick oxygen-ion conductive solid electrolyte layer, printing with a paste may be repeated a plurality of times.

In the case of a gas sensor element of a reference-gas introduction type, the thickness of the oxygen-ion conductive solid electrolyte layer is preferably 0.5 mm to 2 mm (more preferably 0.7 mm to 1.5 mm, most preferably 0.9 mm to 1.3 mm). When the thickness is less than 0.5 mm, the oxygen-ion conductive solid electrolyte layer may fail to have sufficient mechanical strength. When the thickness is in excess of 2 mm, the thermal capacity of the gas sensor element increases possibly causing an impairment in sensitivity at low temperature.

The present invention is characterized in that a mean or average grain size of zirconia is not greater than "2.5 μm". The "mean or average grain size" is obtained on the basis of a photograph of the surface of the solid electrolyte layer photographed at a magnification of 5000 using a scanning electron microscope (hereinafter referred to as a "SEM photograph"). By photographing a back-reflection electron image (hereinafter referred to as a "BEI image") by means of an SEM, grains of different compositions can be photographed in different colors or densities. When the maximum diameter of each grain in an SEM photograph is taken as the size of the grain, the mean size of all zirconia grains contained in a unit square measuring 5 cm×5 cm in the photograph is called a first mean grain size. Five first mean grain sizes are obtained respectively from five SEM photographs corresponding to five different fields of view (surface) on the same solid electrolyte layer and are then averaged so as to obtain a second mean grain size. This second mean grain size serves as the "mean grain size" or rather "average grain size" defined in the present invention.

As seen from the autoclave test results which will be described later in the "Example" section, when the mean grain size of zirconia is in excess of 2.5 μm, the solid electrolyte layer fails to exhibit sufficient durability. By maintaining a mean zirconia grain size of not greater than 2.5 μm, the growth of zirconia grains within the solid electrolyte layer is effectively suppressed, thereby suppressing phase transition of zirconia which would otherwise result from exposure to temperature variations involved in a firing step or thermal cycle. Even when phase transition occurs partially, cracking can be suppressed since stress is readily dispersed. The mean grain size of zirconia is controlled preferably to 0.1 μm to 2.3 μm, more preferably 0.3 μm to 2.0 μm. By attaining such a range of mean grain size, cracking of the solid electrolyte layer can be suppressed.

The above-mentioned grain size distribution of zirconia contained in the solid electrolyte layer is preferably 0.5 μm to 5 μm (more preferably 0.5 μm to 4.2 μm, particularly preferably 0.5 μm to 3.5 μm). Even when the mean grain size is not greater than 2.5 μm, inclusion of a grain having a maximum grain size in excess of 5 μm may cause cracking.

In view of suppression of cracking, preferably, 50% to 100% (more preferably 60% to 100%, particularly preferably 70% to 100%) of zirconia grains contained in a unit square corresponding to each of five fields of view observed on the respective SEM photographs have a maximum grain size of not greater than 3 μm.

Particularly preferably, in view of suppression of cracking, the mean grain size of zirconia is not greater than 2.5 μm, zirconia grains have a maximum grain size of not greater than 5 μm, and 50% to 100% of zirconia grains contained in a unit square corresponding to each of five fields of view observed on the respective SEM photographs have a maximum grain size of not greater than 3 μm.

Zirconia grains contained in the solid electrolyte layer include those assuming a tetragonal phase (hereinafter referred to as the "T phase"), those assuming a monoclinic phase (hereinafter referred to as the "M phase"), and those assuming a cubic phase (hereinafter referred to merely as the "C phase"). The mean grain size of grains assuming the T phase is not greater than 2.5 μm (more preferably 0.1 μm to 2.3 μm, particularly preferably 0.3 μm to 2.0 μm). The T phase is apt to undergo transition to the M phase at an ambient temperature of about 200° C. This phase transition is accelerated with humidity and involves a volume change. Thus, by achieving a mean grain size of not greater than 2.5 μm with respect to grains assuming the T phase, phase transition of zirconia is suppressed which would otherwise result from exposure to temperature variations involved in a firing step or thermal cycle. The mean grain size of grains assuming the T phase is calculated in a manner similar to that for calculating the mean grain size of zirconia described above. Grains assuming the T phase can be differentiated from those assuming other phases by utilizing a BEI image as described above.

Preferably, zirconia is contained in the solid electrolyte layer in the form of stabilized zirconia or partially stabilized zirconia. Particularly preferably, partially stabilized zirconia is contained in a large amount. This makes zirconia less susceptible to phase transition which would otherwise result from exposure to temperature variations involved in the firing step or thermal cycle. Also, physical properties, such as mechanical strength, toughness and thermal-impact resistance, of the solid electrolyte layer are improved. Notably, when the zirconia content of the solid electrolyte layer is taken as 100% by mole, the solid electrolyte layer preferably contains a stabilizer in an amount of 2 to 9% by mole, more preferably 4% to 9% by mole. Examples of such a stabilizer include yttria, magnesia and calcia, and yttria is preferred.

As described above, by including insulating ceramic and zirconia in the solid electrolyte layer and by achieving a mean zirconia grain size of not greater than 2.5 μm, cracking can be suppressed. According to a second aspect of the present invention, the mean grain size of insulating ceramic contained in the solid electrolyte layer is not greater than 1.0 μm to thereby enhance the effect of suppressing cracking. The mean grain size of the insulating ceramic is preferably 0.05 μm to 0.8 μm, more preferably 0.1 μm to 0.6 μm. As the mean grain size of insulating ceramic is reduced, the mean grain size of zirconia can be further reduced. The mean grain size of insulating ceramic can be calculated in a manner similar to that for calculating the mean grain size of zirconia.

The insulating-ceramic or zirconia content of the solid electrolyte layer can be obtained not only by conventional chemical analysis, but also by image analysis of electron photomicrographs. For example, a BEI image, which is photographed by use of an SEM in the same manner as described above, is scanned by means of a scanner to obtain electronic information regarding the image. On the basis of the electronic information, an area ratio between insulating-ceramic grains and zirconia grains is obtained by use of an image analyzer (for example, LUZEX FS, product of NIRECO). On the basis of the thus-obtained area ratio, a theoretical volume ratio is calculated by approximation, and the thus-obtained volume ratio is converted to a content of the insulating ceramic.

The ceramic laminate of the present invention can be used in a laminated oxygen sensor cell comprising the solid electrolyte layer and a pair of electrode layers formed on the solid electrolyte layer. In a conventional laminated oxygen sensor element, the solid electrolyte layer is made of zirconia, and the substrate is made of insulating ceramic (for example, alumina) so as to effect electrical insulation. As a result, the conventional laminated oxygen sensor element is apt to suffer cracking of the solid electrolyte layer due to thermal stress that arises between the solid electrolyte layer and the substrate, as well as phase transition of zirconia, in association with temperature variations involved in a firing step or thermal cycle. By employing the ceramic laminate of the present invention, the oxygen sensor element can effectively suppress the cracking problem. The pair of electrode layers may be formed on the same side of the solid electrolyte layer or on the respective opposite sides of the solid electrolyte layer.

The reference electrode and the measuring electrode are formed on the corresponding opposite sides of the solid electrolyte layer. Gas under measurement comes into contact with the measuring electrode, while reference gas comes into contact with the reference electrode. As a result, an electromotive force is induced according to an oxygen concentration difference between the electrodes by an oxygen concentration cell effect.

In the case of the oxygen sensor element of a reference-oxygen self-generation type (ICP type), the thickness of the solid electrolyte layer is preferably not less than 10 μm to 70 μm (more preferably 20 μm to 60 μm, most preferably 30 μm to 50 μm). When the thickness is less than 10 μm, the durability of the solid electrolyte layer becomes insufficient. In order to form a thick solid electrolyte layer, printing with a paste must be repeated a plurality of times, thereby impairing working performance. Thus, the thickness is preferably not greater than 70 μm.

DESCRIPTION OF REFERENCE NUMERALS

1, 11: substrate (alumina)

1*b*, 11*a*: first substrate (alumina)

Figure 1:
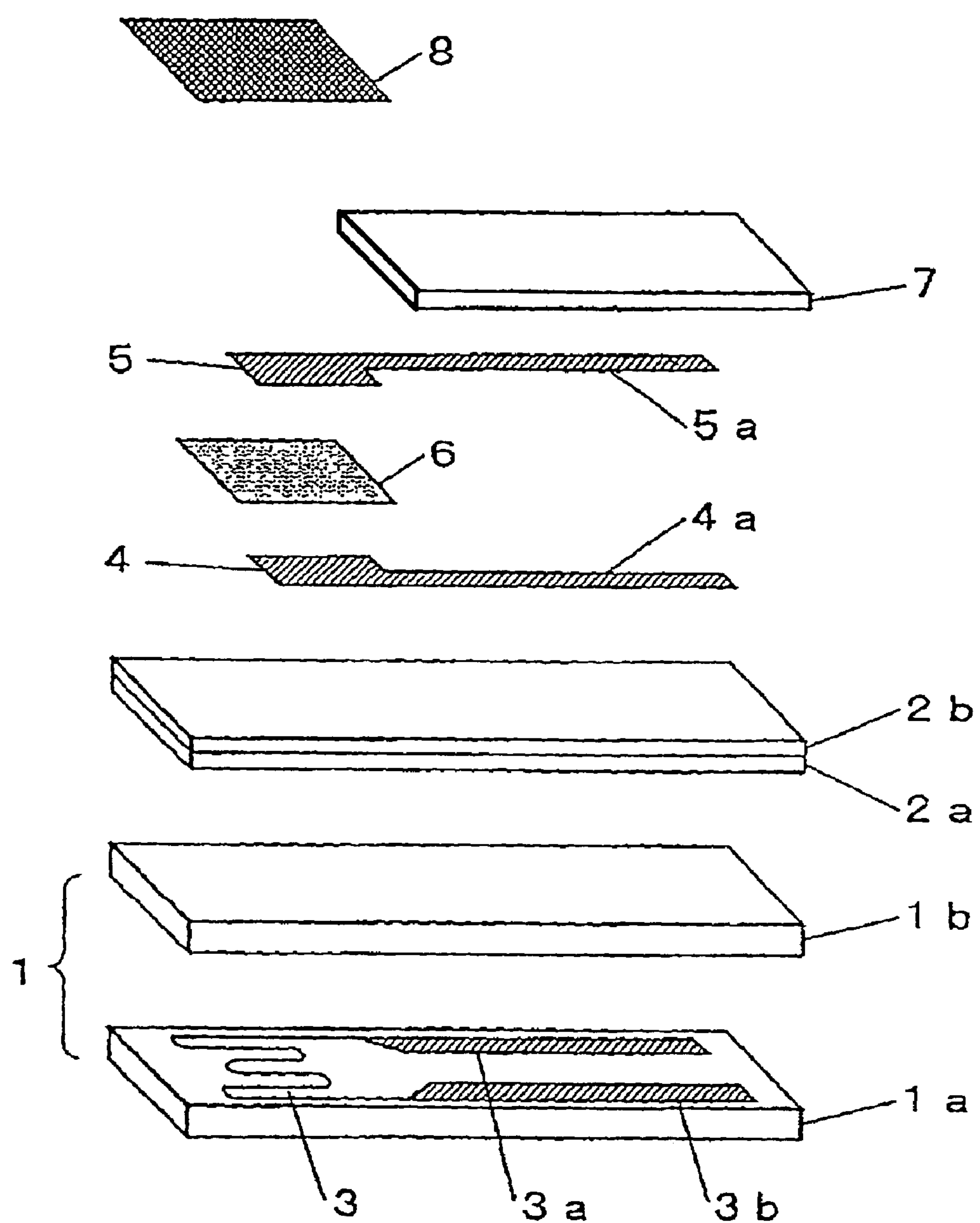
FIG. 1 is a perspective and schematic view of an embodiment of a gas sensor, comprising a solid electrolyte bonded or layer (2) containing alumina grains according to the invention, with other disassembled parts that form a gas sensor laminate.

1*a*, 11*b*: second substrate (alumina)
2*a*: first intermediate layer
2*b*: second intermediate layer
3, 15: heating portion
3*a*, 3*b*, 15*a*, 15*b*: heater lead portion
18*a*, 18*b*: heater lead wire
4, 31*a*: oxygen-reference sensing electrode
4*a*, 31*b*: lead portion for oxygen-reference electrode
5, 32*a*: measuring electrode
5*a*, 32*b*: lead portion for measuring-electrode
6, 12: oxygen-ion conductive solid electrolyte layer
7, 16: alumina ceramic layer for reinforcement
8, 14: poisoning prevention layer for protecting electrode
71: reference-electrode lead wire
72: measuring-electrode lead wire

DESCRIPTION OF THE PREFERRED EMBODIMENTS

The present invention will next be described in detail by way of the following Examples relating to fabrication of an gas sensor element. However, the present invention should not by construed as being limited thereto.

EXAMPLE 1

A gas sensor element of a reference-oxygen self-generation type was fabricated. The fabrication procedure will be understood with reference to FIG. 1, which schematically shows the gas sensor element in an exploded or rather disassembled manner.

(1) Fabrication of an Alumina Green Sheet Which Becomes a Substrate Upon Firing

Butyral resin and dibutyl phthalate with respectively predetermined amounts were added to alumina powder serving as an insulating ceramic to thereby prepare a paste. The paste was sheeted through doctor-blading to obtain an alumina green sheet (a) which became a substrate (1*a*) upon firing and an alumina green sheet (b) which became a substrate (1*b*) upon firing, each serving as an unfired substrate and having a thickness of 0.4 mm. The substrates (1*a*), (1*b*) constitute an alumina substrate (1).

(2) Formation of Heater Pattern

An alumina-containing platinum paste was applied onto the surface of the alumina green sheet so as to form a heater pattern (having a thickness of about 20 μm) which became a heating portion (3) and heater lead portions (3*a*), (3*b*) upon firing, followed by drying. Platinum lead wires were disposed on the alumina green sheet (a). The alumina green sheet (b) was superposed under pressure on the alumina green sheet such that the heater pattern was sandwiched therebetween and co-fired with the alumina sheets.

(3) Formation of Films Which Become First and Second Intermediate Layers Upon Firing 80 Parts by weight (hereinafter referred to as parts) of alumina powder and 20 parts of zirconia material powder which contained 5.5% by mole yttria as a stabilizer were mixed. To the resultant mixture, butyral resin and dibutyl phthalate were added in respectively predetermined amounts to thereby prepare a paste. The paste was applied onto the surface of the alumina green sheet (b) so as to form a first film (having a thickness of about 20 μm) which became a first intermediate layer (2*a*) upon firing. Subsequently, a second film (having a thickness of about 20 μm) which became a second intermediate layer (2*b*) upon firing was formed on the first film in a manner similar to that of formation of the first film except that 50 parts of zirconia material powder was employed.

(4) Formation of Oxygen-reference Electrode Pattern and Disposition of Oxygen-reference Electrode Lead Wires A oxygen-reference electrode pattern which became a oxygen-reference electrode (4) and an oxygen-reference electrode lead portion (4*a*) upon firing was printed on the second film using a platinum paste, followed by drying to form a film having a thickness of 20 μm. Then, platinum wires were disposed so as to serve as oxygen-reference electrode lead wires for outputting a sensor output signal.

(5) Formation of Unfired Oxygen-ion Conductive Solid Electrolyte Layer Which Becomes an Oxygen-ion Conductive Solid Electrolyte Layer Upon Firing 90 parts by weight of a high purity zirconia powder having a contamination material of less than 0.1%, which powder contained 5.5% by mole yttria as a stabilizer, and 10 parts by mass of alumina powder having a contamination material of less than 0.005% by weight was mixed. To the resultant mixture, butyl carbitol, dibutyl phthalate, a dispersant and a binder were added and mixed in respectively predetermined amounts to thereby prepare a zirconia paste. The zirconia paste was applied to the oxygen-reference electrode pattern to thereby form an unfired oxygen-ion conductive solid electrolyte layer having a thickness of 15 μm, followed by drying. Subsequently, the zirconia paste was further applied similarly twice to thereby form a thicker unfired oxygen-ion conductive solid electrolyte layer (having a total thickness of 45 μm) which became an oxygen-ion conductive solid electrolyte layer (6) upon firing.

(6) Formation of Measuring Electrode Pattern and Disposition of Measuring-electrode Lead Wires A measuring-electrode pattern (which became a measuring-electrode 5 and a measuring-electrode lead portion 5*a* upon firing) containing a paste of platinum was printed on the surface of the unfired oxygen-ion conductive solid electrolyte layer to form a film having a thickness of 20 μm, followed by drying. Then, lead wires of platinum were disposed so as to serve as measuring-electrode lead wires for outputting an output signal from a electrolyte cell comprising the electrolyte and the electrodes.

(7) Formation of Alumina Film Which Becomes an Alumina Ceramic Layer Upon Firing The alumina paste prepared in (1) was applied onto the measuring-electrode pattern and the unfired oxygen-ion conductive solid electrolyte layer, followed by drying, to form a film having a thickness of about 20 μm. Subsequently, the alumina paste was applied similarly twice to thereby form an alumina film (having a total thickness of about 60 μm) which became an alumina ceramic layer (7) upon firing.

(8) Debinding and Firing

The laminate formed through the steps (1) to (7) was placed at a temperature of 420° C. for 2 hours in the atmosphere for debinding (binder removal). Subsequently, the laminate was co-fired at a temperature of 1520° C. for 1 hour in the atmosphere. The thus-fabricated laminate (a gas sensor element); particularly, end faces thereof were visually inspected. The visual inspection reveals whether the gas sensor element is free of cracking, separation of layers and warpage.

The alumina paste prepared in the step (1) was applied to an alumina sheet in forming a film measuring 30 mm (length)×10 mm (width)×1 mm (thickness), followed by debinding and firing in a manner similar to that of step (8). The resultant test piece was measured for density by an Archimedian method and was found to be 3.63 g/cm$^3$; i.e., a relative density with respect to a theoretical density of 91.4%. The relative density of the alumina ceramic layer of the gas sensor element was around 91.4%.

EXAMPLE 2

Gas sensor elements were fabricated and studied for the interrelation between the alumina content of the oxygen-ion conductive solid electrolyte layer and the internal resistance of the oxygen-ion conductive solid electrolyte layer.

Alumina powder with 99.997% purity and zirconia material powder with 99.95% purity, which contained 5.5% by mole yttria were mixed according to Table 1. To the resultant mixture, butyl carbitol, dibutyl phthalate, a dispersant, and an organic binder with the respectively predetermined amounts were added to thereby prepare a zirconia paste. By using the zirconia paste, gas sensor elements (1) to (14) were fabricated in a manner similar to that of Example 1. The gas sensor elements (1) to (14) were fitted into respective protection tubes and were exposed to combustion gas generated by combustion of town gas while the heater embedded in the alumina substrate was not energized. On the basis of sensor output, the internal resistance of some gas sensor elements selected from the test pieces (1) to (14) was determined. The temperature of the combustion gas wherein the test piece is placed was measured at a burner port of the gas and set at 600° C. The results are as follows. When the oxygen-ion conductive solid electrolyte layer contained no alumina, the internal resistance that was measured across the electrodes sandwiching the solid electrolyte was approximately 0.2 kΩ. The internal resistance was approximately 0.4 kΩ when the alumina content was 30%; approximately 0.6 kΩ at an alumina content of 50%; approximately 0.6 kΩ at 60%; approximately 0.7 kΩ at 70%; and 25–40 kΩ at 80%. (Therein, the thickness of the fired solid electrolyte layer sandwiched by the two electrodes each having an area of about 9 $mm^2$ was about 40 Ωm.) Thus, the maximum limit of the alumina content in the oxygen-ion conductive solid electrolyte layer is considered to be 80% for a gas sensor, because most gas sensors need a resistance across the electrodes of less than 50 kΩ, preferably less than 10 kΩ.

Then, at an elevated temperature of 800° C., a specific resistance of the solid electrolyte per se of test piece (8) in Table 1 was determined based on a Cole-Cole plot; the specific resistance was about 2 Ωm.

Note that in Tables 1 and 2 the samples marked * may not perform well in a very severe environment as modeled in the autoclave test, such as for a gas sensor for an internal combustion engine required to undergo −20° C. to 1000° C. thermal cycles. Nevertheless, these examples may be used in other applications and are not necessarily excluded from the scope of the invention.

EXAMPLE 3

Autoclave Durability Test:

Fired gas sensor elements (1) to (14) obtained through steps (1) to (8) of Example 1 were placed in an autoclave for 6 hours at a temperature of 200° C. a humidity of 100%, and a pressure of 15 atm. Subsequently, water-soluble red ink was applied to the gas sensor elements (1) to (14) so as to color cracks, if caused, thereby evaluating durability thereof. The results are shown in Table 1. In Table 1, "O" indicates that no cracks were generated, and "X" indicates that cracks were generated.

As seen from Table 1, by employing an alumina content range specified in the present invention, cracking does not occur.

EXAMPLE 4

Autoclave Durability Test On Two Solid Electrolytes (co-fired)

A laminate composed of two solid electrolyte layers (unfired solid electrolyte layers) of different compositions was subjected to integral firing, thereby forming each of test pieces 1 to 14 as shown in Table 2. Test pieces 1 to 14 were subjected to an autoclave durability-test so as to be evaluated for durability.

(1) Fabrication of Test Pieces, Each Composed of 2 Different Solid Electrolyte Layers The lower layer of the laminate was formed by printing using a zirconia paste which was prepared in a manner similar to that described in step (5) of Example 1 except that alumina was not contained (the mean grain size of zirconia material powder was 1.0 μm). The printed layer measured 0.04 mm (thickness)×6 mm×6 mm and became a solid electrolyte layer upon firing. The upper layer of the laminate was formed by printing on the unfired lower layer using a

TABLE 1

| | | Characteristics of Solid Electrolyte Layer (upper layer) | | | |
|---|---|---|---|---|---|
| Oxygen Sensor Element | Firing temp. | Zirconia Content (% by weight) | Alumina Content (% by weight) | Autoclave Accelerated Durability | Solid Electrolyte Characteristics (internal resistance) |
| 1 | 1480 | 90 | 10 | O | O |
| 2 | 1540 | 90 | 10 | O | O |
| 3 | 1540 | 90 | 10 | O | O |
| 4 | 1480 | 80 | 20 | O | O |
| 5 | 1480 | 70 | 30 | O | O |
| *6 | 1560 | 70 | 30 | X | O |
| 7 | 1480 | 60 | 40 | O | O |
| 8 | 1490 | 50 | 50 | O | O |
| 9 | 1480 | 40 | 60 | O | O |
| 10 | 1480 | 30 | 70 | O | O |
| *11 | 1660 | 30 | 70 | X | O |
| 12 | 1480 | 20 | 80 | O | O |
| *13 | 1480 | 10 | 90 | X | X |
| *14 | 1540 | 100 | 0 | X | O |

zirconia paste containing alumina and zirconia such that their contents differed among test pieces 1 to 14 (:Table 2 shows the mean grain size of zirconia material powder and that of alumina material powder). The printed layer measured 0.04 mm (thickness)×5 mm×5 mm and became a solid electrolyte layer upon firing. The laminate composed of these unfired solid electrolyte layers was fired in the atmosphere at a temperature shown in Table 2 (for 2 hours).

The thus-fired test pieces 1 to 14 were examined for the mean zirconia grain size of the upper layer, which is calculated by the previously mentioned method. The results are shown in Table 2. Table 2 also shows the zirconia and alumina contents of the upper solid electrolyte layer as measured when the total amount of zirconia and alumina is taken as 100% by weight. In Table 2, the upper solid electrolyte layer of test piece 14 did not contain alumina.

indicating no occurrence of cracking. Thus, it is considered that, in a solid electrolyte layer which contains alumina and in which the mean grain size of zirconia is not greater than 2.5 μm, phase transition of zirconia may be effectively suppressed.

(3) Electron Micrographs

Figure 5:
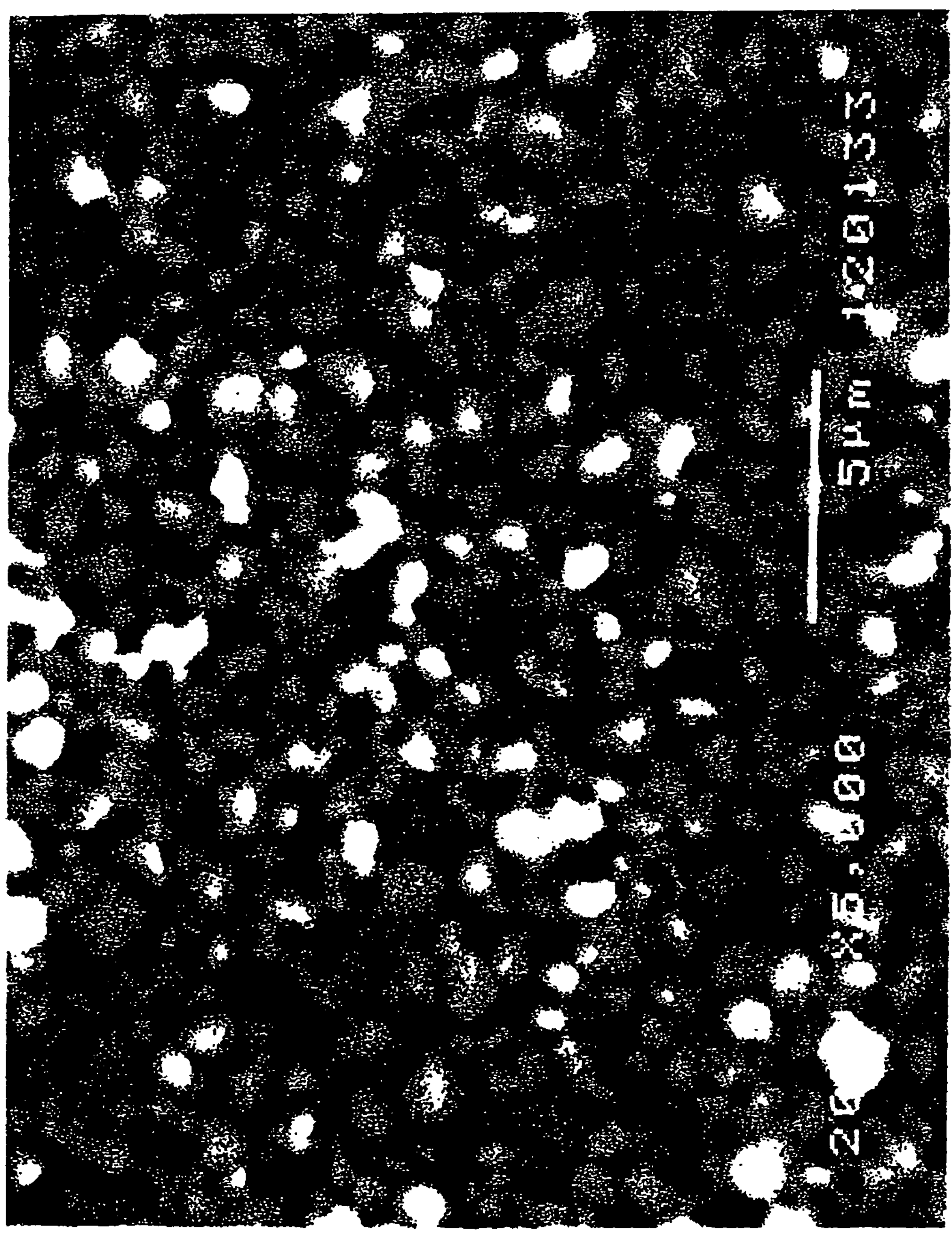
FIG. 5 is an electron micrograph of a surface of a solid electrolyte layer containing alumina grains (:test piece 2) according to the invention, taken at a magnification of 5000.
Figure 6:
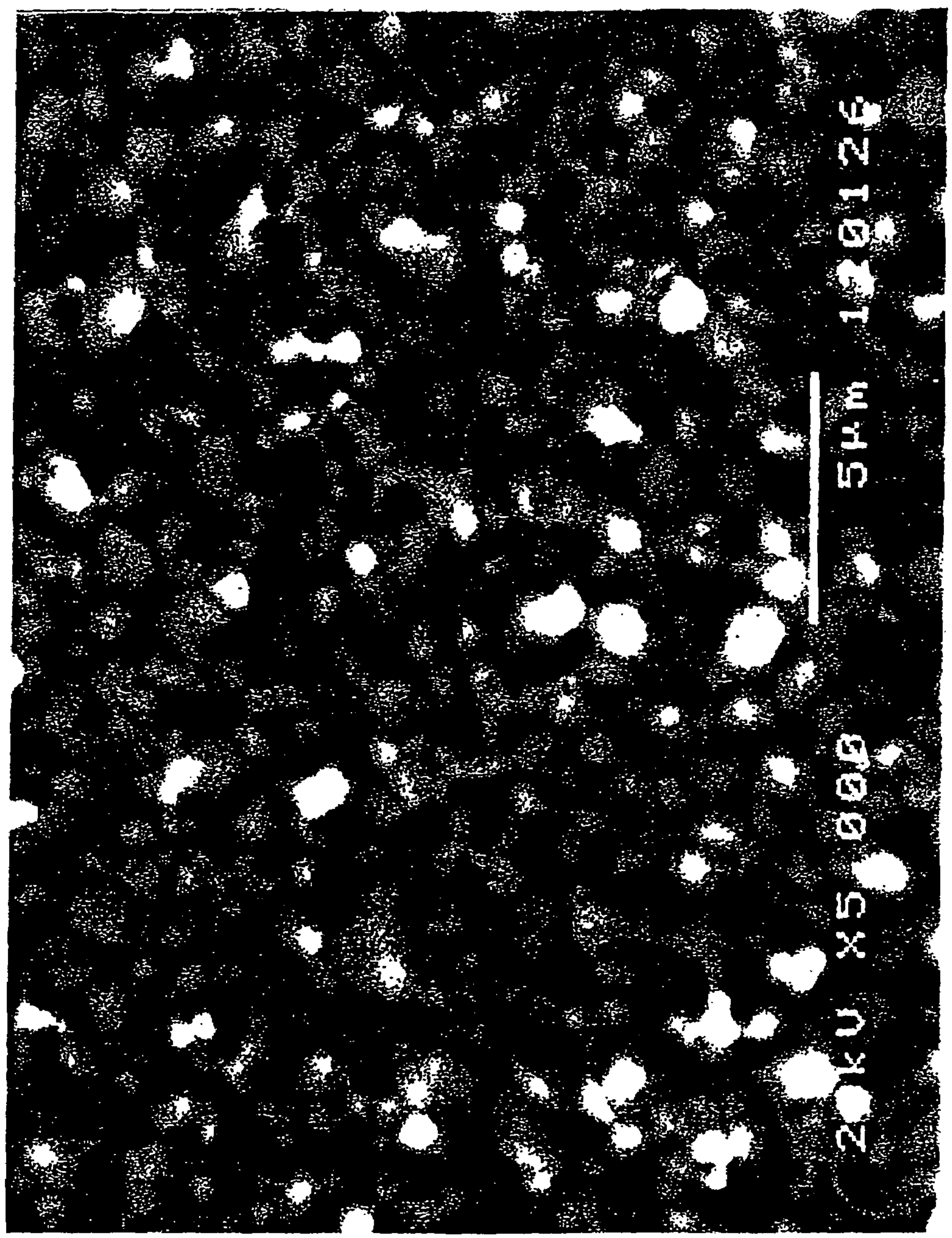
FIG. 6 is an electron micrograph of a surface of a solid electrolyte layer containing alumina grains (:test piece 3) according to the invention, taken at a magnification of 5000.
Figure 7:
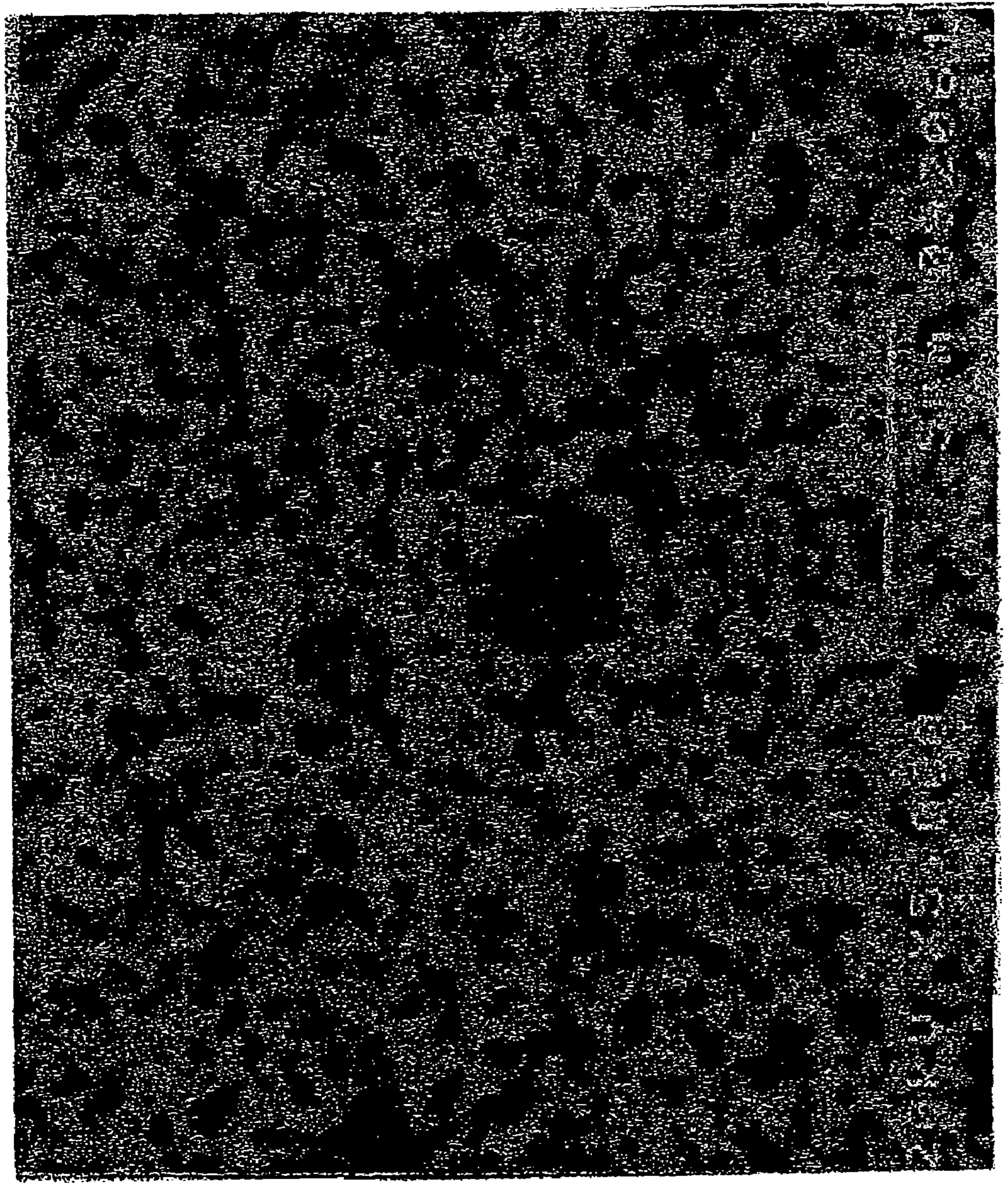
FIG. 7 is an electron micrograph of a surface of a solid electrolyte layer containing alumina grains (:test piece 5) according to the invention, taken at a magnification of 5000.
Figure 8:
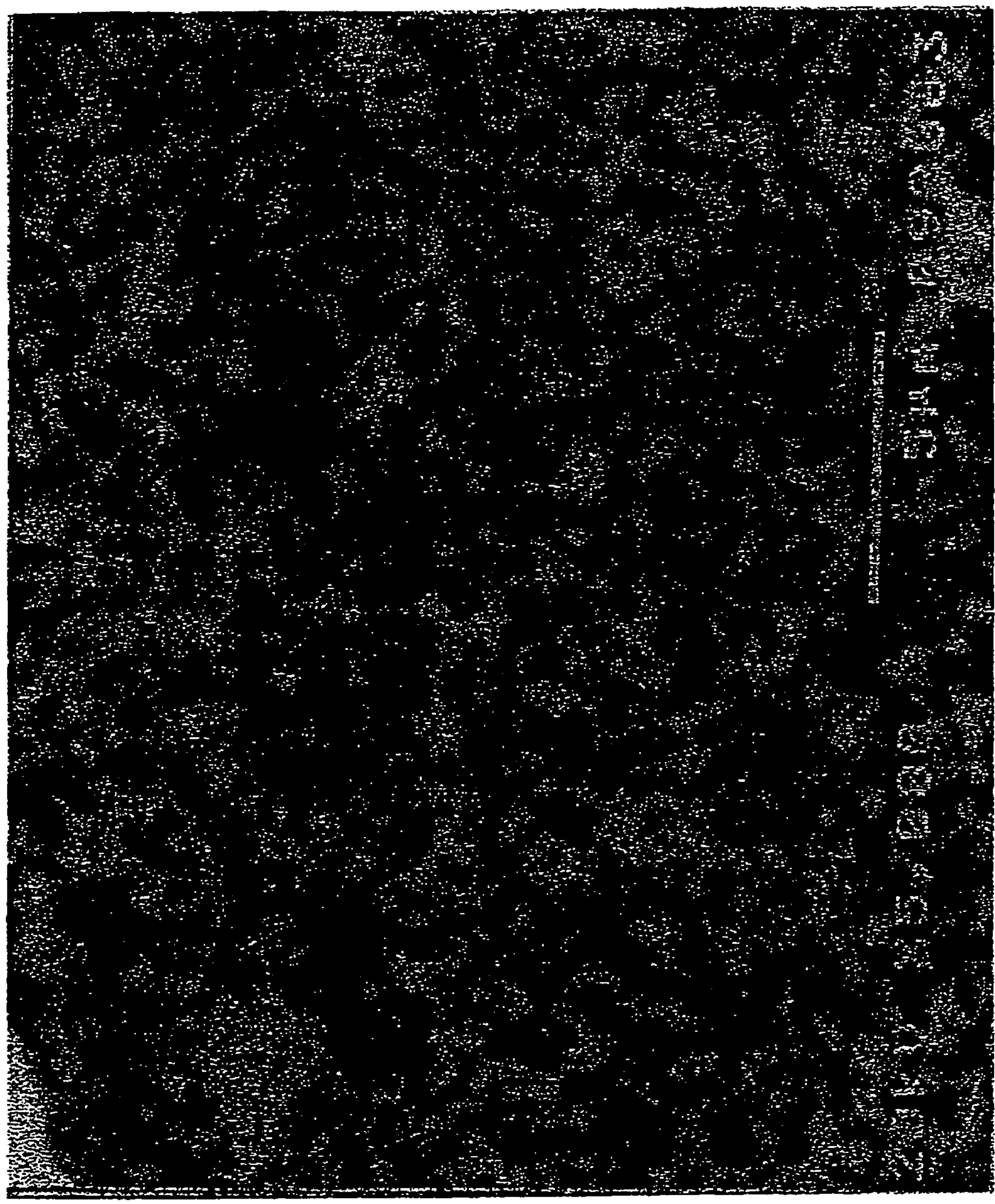
FIG. 8 is an electron micrograph of a surface of a solid electrolyte layer containing alumina grains (:test piece 8) according to the invention, taken at a magnification of 5000.

The surface of each of test pieces 1, 2, 3, 5 and 8 fabricated in Example 4 was photographed at a magnification of 5000 by means of an electron microscope (JSM-5410, product of JEOL Ltd.). FIGS. 4 to 8 show the photographs. Specifically, FIG. 4 corresponds to test piece 1; FIG. 5 corresponds to test piece 2; FIG. 6 corresponds to test piece 3; FIG. 7 corresponds to test piece 5; and FIG. 8 corresponds to test piece 8. For comparison, the surface of test piece 14; i.e., the surface of the solid electrolyte layer which did not contain alumina was similarly photographed

TABLE 2

| | Characteristics of Material Powder | | | Characteristics Of Solid Electrolyte Layer (upper layer) | | | |
|---|---|---|---|---|---|---|---|
| Test Piece | Mean grain size of zirconia material powder (μm) | Mean grain size of alumina material powder (μm) | Firing temp. | Mean grain size of zirconia (μm) | Zirconia content (% by weight) | Alumina content (% by weight) | Autoclave accelerated durability |
| 1 | 0.6 | 0.1 | 1480 | 1.8 | 90 | 10 | o |
| 2 | 0.6 | 0.1 | 1540 | 1.8 | 90 | 10 | o |
| 3 | 0.9 | 0.3 | 1540 | 2.0 | 90 | 10 | o |
| 4 | 0.6 | 0.3 | 1480 | 1.5 | 80 | 20 | o |
| 5 | 0.6 | 0.3 | 1480 | 1.3 | 70 | 30 | o |
| *6 | 2.3 | 1.5 | 1560 | *2.6 | 70 | 30 | x |
| 7 | 0.6 | 0.3 | 1480 | 1.2 | 60 | 40 | o |
| 8 | 0.6 | 0.4 | 1490 | 1.6 | 50 | 50 | o |
| 9 | 0.6 | 0.3 | 1480 | 0.9 | 40 | 60 | o |
| 10 | 0.6 | 0.3 | 1480 | 0.8 | 30 | 70 | o |
| *11 | 2.5 | 2.5 | 1560 | *3.0 | 30 | 70 | x |
| 12 | 0.6 | 0.3 | 1480 | 0.8 | 20 | 80 | o |
| *13 | 2.3 | 0.3 | 1480 | *2.8 | 10 | 90 | x |
| *14 | 1.2 | — | 1540 | 2.4 | 100 | *0 | x |

(2) Autoclave Durability Test

The test pieces were placed in an autoclave for 6 hours at a temperature of 200° C., a humidity of 100%, and a pressure of 15 atm. Subsequently, water-soluble red ink was applied to the test pieces so as to color cracks, if caused, thereby evaluating durability thereof on the basis of the degree of coloration. The results are shown in Table 2. In Table 2, the symbol "o" indicates that no cracking occurred, and the symbol "x" indicates the cracking occurred. As seen from Table 2, coloration was observed in test pieces 6, 11 and 13 in which the mean zirconia grain size as measured after was in excess of 2.5 μm, and in test piece 14 in which the solid electrolyte layer did not contain alumina, indicating the occurrence of cracking.

Figure 2:
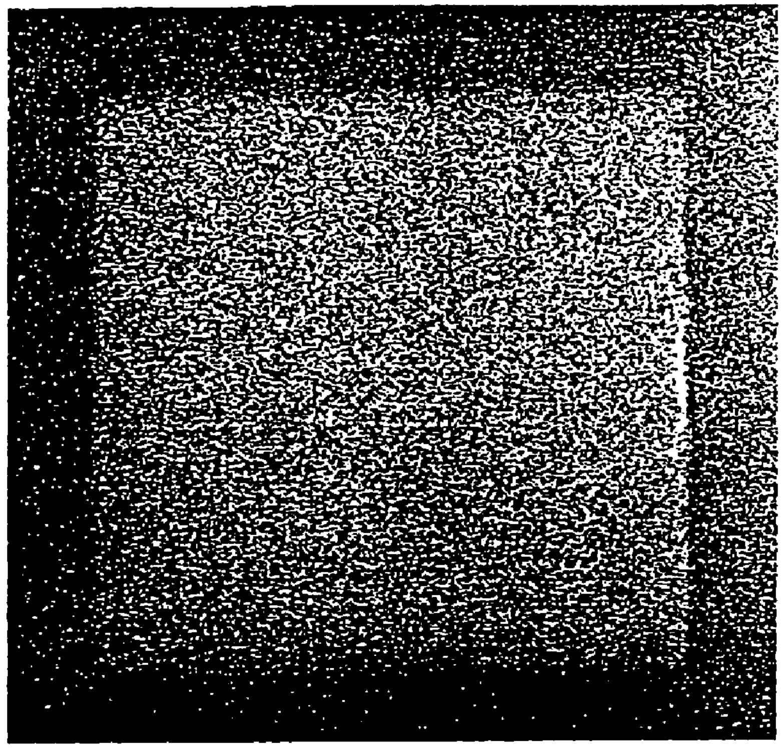
FIG. 2 is a photograph taken after subjecting to an autoclave durability test two solid electrolyte layers bonded by co-firing(:test piece 2), wherein a top layer is a solid electrolyte layer containing alumina grains according to the invention and showing no induced cracks, and a bottom layer is a solid electrolyte layer having no alumina grains and showing induced cracks.
Figure 3:
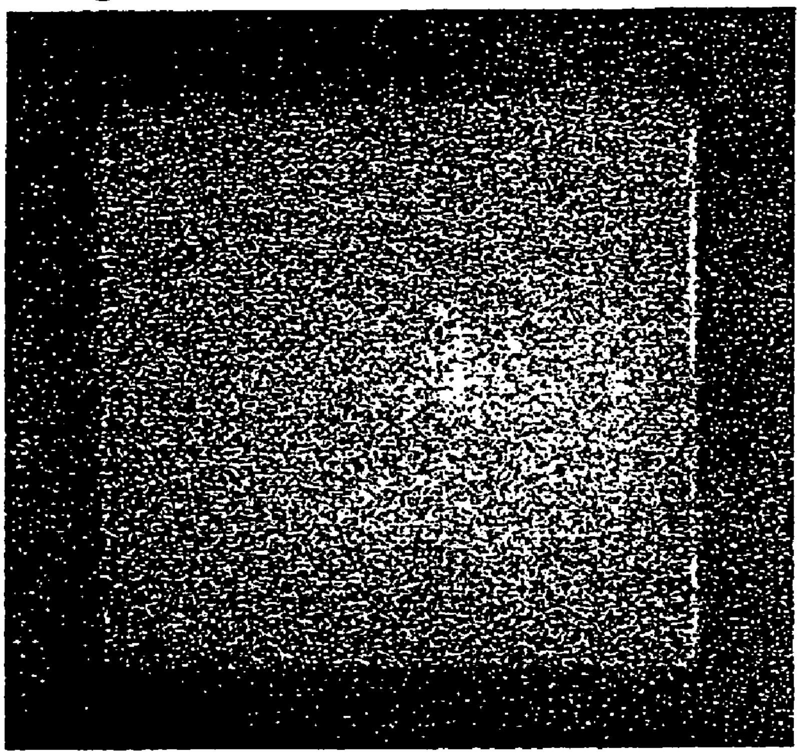
FIG. 3 is a photograph taken after subjecting to an autoclave durability test two solid electrolyte layers bonded by co-firing (:test piece 3), wherein a top layer is a solid electrolyte layer containing alumina grains different in size from test piece 2 according to the invention and showing no induced cracks, and a bottom layer is a solid electrolyte layer containing no alumina grains and showing induced cracks.
Figure 4:
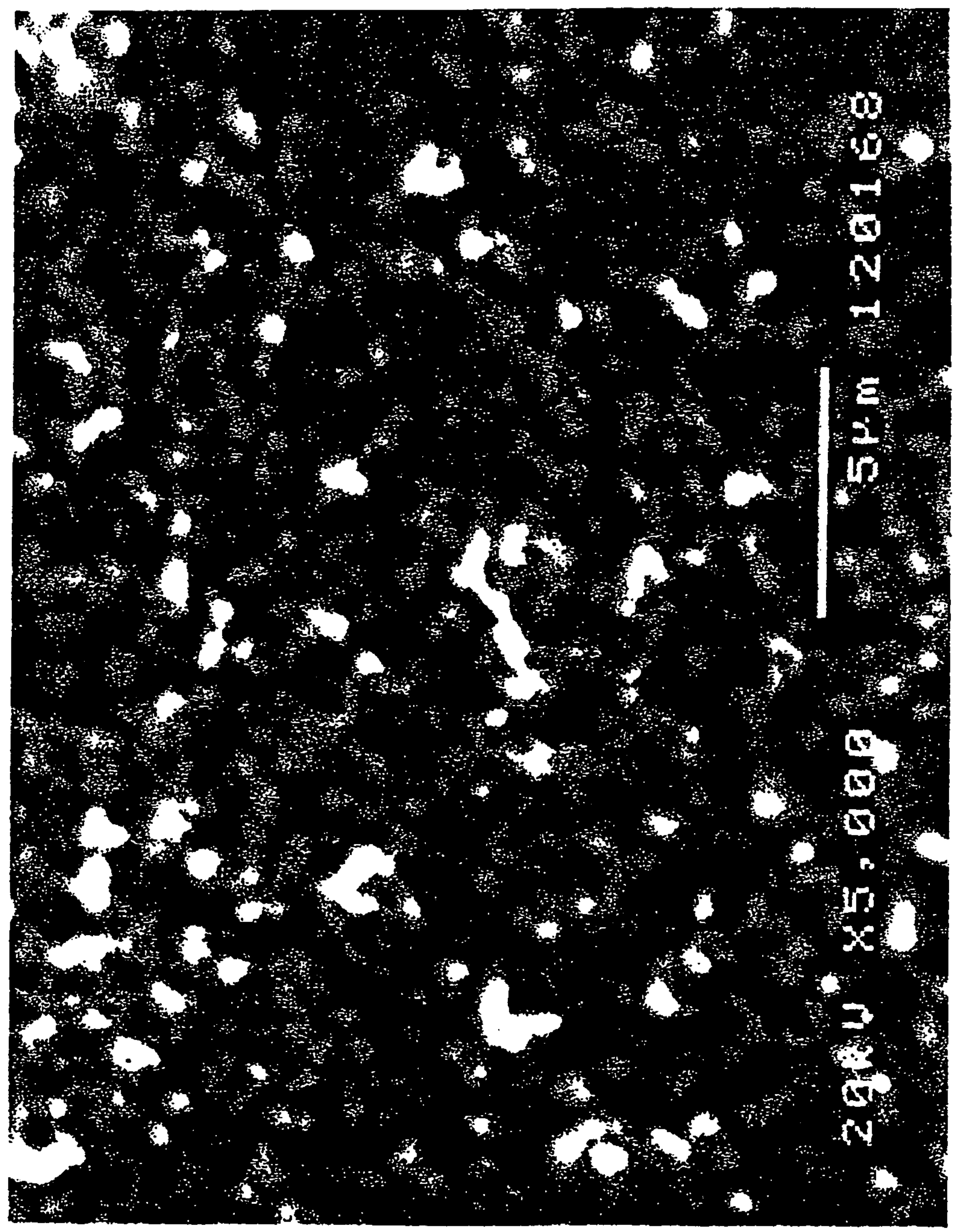
FIG. 4 is an electron micrograph of a surface of a solid electrolyte layer containing alumina grains (:test piece 1) according to the invention, taken at a magnification of 5000.
Figure 9:
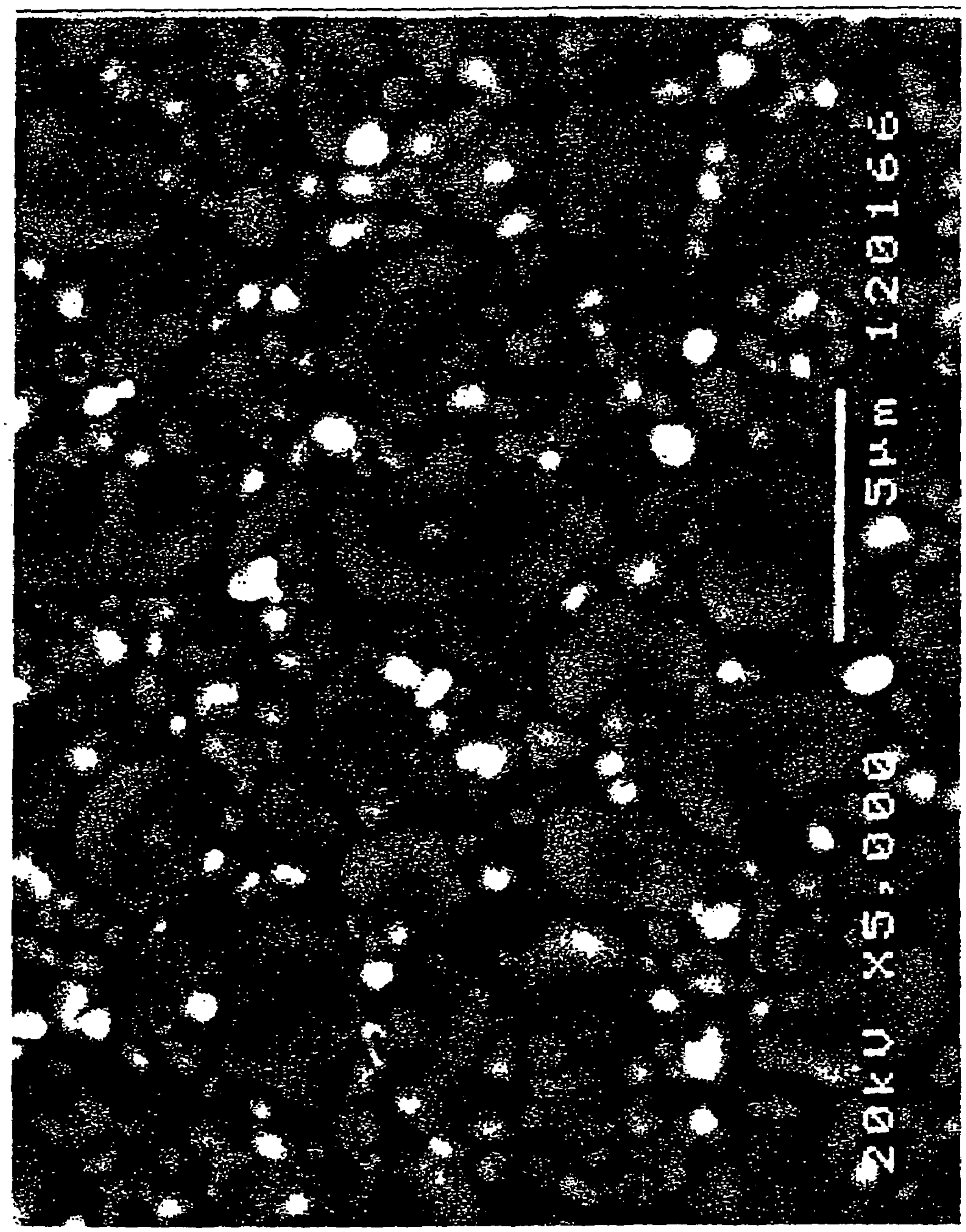
FIG. 9 is an electron micrograph of a surface of a solid electrolyte layer containing alumina grains (:test piece 14) containing no alumina, taken at a magnification of 5000.
Figure 10:
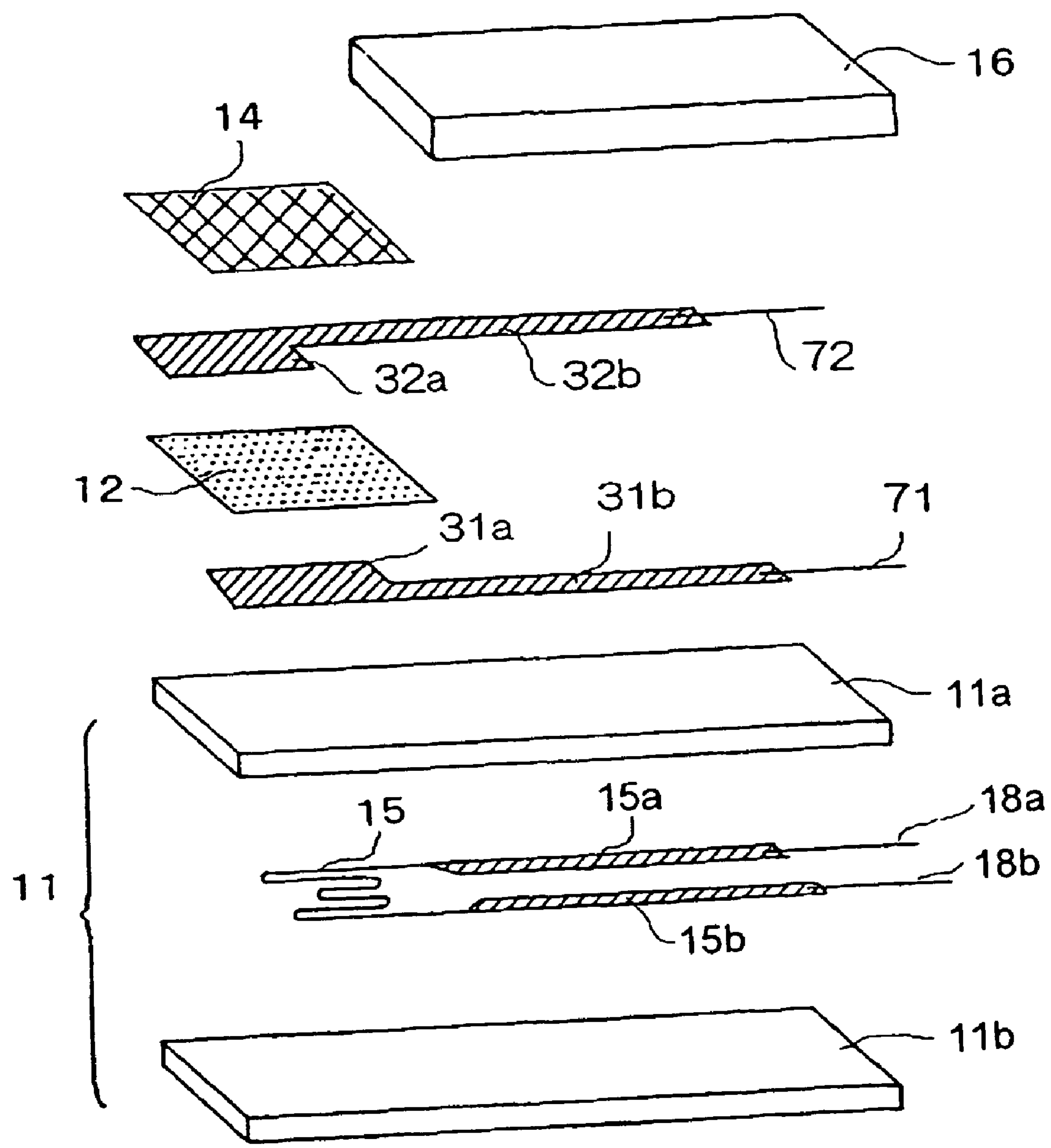
FIG. 10 is a perspective and schematic view of another embodiment of a gas sensor with a solid electrolyte body or layer (26) according to the invention, with other disassembled parts that form another gas sensor laminate.

FIGS. 2 and 3 show photographs of test pieces 2 and 3 which have undergone the autoclave durability test. In FIGS. 2 and 3, a central white portion is the solid electrolyte layer (upper layer) which contains zirconia and alumina, and a peripheral portion around the upper layer is the solid electrolyte layer (lower layer) which does not contain alumina. The peripheral portion assumes a dark color since cracks are colored by the colorant. As seen from these figures, coloration is hardly observed in any test piece having a solid electrolyte layer which contains alumina and in which the mean grain size of zirconia is not greater than 2.5 μm, at a magnification of 5000 by means of the electron microscope. The photograph is shown in FIG. 9.

In FIGS. 4 to 8, white grains are of zirconia, and black grains are of alumina. In FIG. 9, black portions are depressions. As seen from these figures, as compared to the mean grain size of zirconia in the solid electrolyte layer of FIG. 9, which does not contain alumina, the mean grain size of zirconia in the case of FIGS. 4 to 8 is suppressed to a significantly low level.

A ceramic laminate according to an aspect of the present invention yields the following advantages. By including high-purity zirconia and high-purity insulating ceramic (particularly alumina) with controlled respective average grain size in a solid electrolyte layer and by maintaining a mean (or average) zirconia grain size of not greater than 2.5 μm and a mean alumina grain size, less than 1.0 μm, respectively, the growth of zirconia grains within the solid electrolyte layer is considerably suppressed, and phase transition of zirconia is suppressed effectively. Also, even when a substrate, a solid electrolyte layer, electrodes, a protection layer, and a heater are integrally fired, cracking of the solid electrolyte layer is suppressed quite effectively. Even after firing, the resultant ceramic laminate is stable in any kind of environment, thereby preventing cracking of the solid electrolyte layer. A fabricating method according to the above aspects of the present invention enables easy, stable fabrication of a ceramic laminate having the above-described excellent performance. Furthermore, when an oxygen sensor element is to be formed using the ceramic laminate of the present invention, the oxygen sensor element may be a thick-film oxygen sensor element of any type, such as an ICP type or reference gas introduction type, or a bulk oxygen sensor.

The present invention is not limited to the above-described embodiments. Numerous modifications and variations of the present invention are possible according to purpose or application without departing from the scope of the invention. For example, the alumina substrate and the oxygen-ion conductive solid electrolyte layer may contain ceramics other than alumina, zirconia and yttria. The electrodes may be formed on one surface of the electrolyte layer or formed in a manner sandwiching the electrolyte. The electrodes can be formed simultaneously at the time of co-firing the electrolyte and the ceramic substrate. Instead of zirconia, hafnia or mixture of zirconia and hafnia may be used for the electrolyte material.

This application is based on Japanese Patent Application Nos. Hei 11-26733 filed Feb. 3, 1999, Hei 11-375808 filed Dec. 28, 1999 and Hei 11-375846 filed Dec. 28, 1999, the disclosures of which are hereby incorporated by reference in their entirety.

What is claimed is:

1. A gas sensor including an electrochemical cell for detecting a gas concentration, comprising an oxygen-ion conductive solid electrolyte layer comprising stabilized or partially stabilized zirconia and alumina grains; metallic electrodes comprising a gas measuring electrode including a lead portion and an oxygen-reference electrode formed on the oxygen-ion conductive solid electrolyte layer; a ceramic substrate mainly comprising alumina laminated with the oxygen ion conductive solid electrolyte layer and including a heater and heater leads embedded in the substrate; and an intermediate ceramic layer comprising zirconia which may be stabilized in part or whole in an amount of 20% by weight or more and alumina, the intermediate layer being disposed between the oxygen ion-conductive solid electrolyte layer and the ceramic substrate and has a thickness of 5 μm to 200 μm, wherein the oxygen-ion conductive solid electrolyte layer contains 10% to 80% by weight of alumina grains, the amount of alumina contained in the intermediate ceramic layer is at least 10% by weight more than in the oxygen-ion conductive solid electrolyte layer, an average grain size of solid electrolyte ceramic grains of stabilized or partially stabilized zirconia contained in the oxygen-ion conductive solid electrolyte layer after firing is not greater than 2.5 μm, and an average grain size of the alumina grains contained in the oxygen-ion conductive solid electrolyte layer after firing is not greater than 1 μm, and wherein the oxygen-ion conductive solid electrolyte layer, the metallic electrodes, the ceramic substrate, and the intermediate layer are integrally co-fired at a sintering temperature of at least 1350° C. to form a laminate.

2. The gas sensor as claimed in claim 1, wherein the oxygen-ion conductive solid electrolyte layer, the metallic electrodes, the ceramic substrate, and the intermediate layer are integrally co-fired at a sintering temperature of 1350° C. to 1600° C. to form a laminate.

3. The gas sensor as claimed in claim 1, wherein the amount of alumina contained in the intermediate ceramic layer is at least 15% by weight more than in the oxygen-ion conductive solid electrolyte layer.

4. The gas sensor as claimed in claim 1, wherein the intermediate layer has an alumina content that is greater than that of the oxygen-ion conductive solid electrolyte layer and less than that of the ceramic substrate.

5. The gas sensor as claimed in claim 1, wherein the intermediate layer has a thickness of 20 μm to 50 μm.

6. The gas sensor as claimed in claim 1, wherein the intermediate layer has a thickness of 5 μm to 50 μm.

7. The gas sensor as claimed in claim 1, wherein the intermediate layer has a thickness of 5 μm to 40 μm.

8. The gas sensor as claimed in claim 1, wherein the intermediate layer comprises two or more intermediate layers having a total thickness of 5 μm to 200 μm.

9. The gas sensor as claimed in claim 8, wherein the intermediate layer closest to the ceramic substrate has an insulating ceramic content higher than that of the intermediate layer closest to the oxygen-ion conductive solid electrolyte layer.

10. The gas sensor as claimed in claim 1, wherein the alumina grain contained in the oxygen-ion conductive solid electrolyte layer is a product formed from alumina having a purity of more than 99.9%.

11. The gas sensor as claimed in claim 1, wherein the alumina grain contained in the oxygen-ion conductive solid electrolyte layer is a product formed from alumina having a purity of more than 99.99%.

12. The gas sensor as claimed in claim 1, wherein the oxygen-ion conductive solid electrolyte layer contains an amount of 20% to 90% by weight of solid electrolyte ceramic.

13. The gas sensor as claimed in claim 1, wherein the solid electrolyte ceramic contained in the oxygen-ion conductive solid electrolyte layer contains a stabilizer in an amount of from 2 to 9% by mole.

14. The gas sensor as claimed in claim 1, wherein the metallic electrodes formed on the oxygen-ion conductive solid electrolyte layer comprise Pt.

15. The gas sensor as claimed in claim 1, wherein said ceramic substrate is an alumina substrate on which the oxygen-ion conductive solid electrolyte layer is formed integrally; said metallic electrodes comprise an oxygen-reference electrode formed integrally on the oxygen-ion conductive solid electrolyte layer, and a gas-measuring electrode formed integrally on a surface of the oxygen-ion conductive solid electrolyte layer opposite the ceramic substrate.

16. The gas sensor as claimed in claim 15, wherein said oxygen-ion conductive solid electrolyte layer contains alumina grains in an amount of 30% to 70% by weight based on the weight of the oxygen-ion conductive solid electrolyte layer.

17. The gas sensor as claimed in claim 1, further comprising a reinforcing ceramic layer having a relative density of 60% to 99.5% formed on the lead portion of the gas measuring electrode on the side of the gas sensor opposite the ceramic substrate.

18. The gas sensor as claimed in claim 17, further comprising a poison-prevention layer formed on a portion of the electrolyte layer and gas-measuring electrode not covered by the reinforcing ceramic layer, for preventing the gas-measuring electrode from being poisoned by a foreign element.

19. The gas sensor as claimed in claim 18, wherein the poison-prevention layer contains spinel.

20. The gas sensor as claimed in claim 17, wherein the reinforcing ceramic layer comprises alumina.

* * * * *